(12) United States Patent
Cheong et al.

(10) Patent No.: US 8,158,023 B2
(45) Date of Patent: *Apr. 17, 2012

(54) BIAXIAL LIQUID CRYSTAL COMPOUND, LIQUID CRYSTAL COMPOSITION COMPRISING THE SAME, AND OPTICAL FILM USING THE SAME LIQUID CRYSTAL COMPOSITION

(75) Inventors: Jae-Ho Cheong, Daejeon (KR); Min-Jin Ko, Daejeon (KR); Myung-Sun Moon, Daejeon (KR); Bum-Gyu Choi, Daejeon (KR); Dae-Ho Kang, Daejeon (KR); Ki-Youl Lee, Daejeon (KR); Yun-Bong Kim, Seoul (KR)

(73) Assignee: LG Chem, Ltd., Seoul (KR)

( * ) Notice: Subject to any disclaimer, the term of this patent is extended or adjusted under 35 U.S.C. 154(b) by 7 days.

This patent is subject to a terminal disclaimer.

(21) Appl. No.: 12/448,877

(22) PCT Filed: Jan. 22, 2008

(86) PCT No.: PCT/KR2008/000390
§ 371 (c)(1),
(2), (4) Date: Jul. 13, 2009

(87) PCT Pub. No.: WO2008/091092
PCT Pub. Date: Jul. 31, 2008

(65) Prior Publication Data
US 2010/0078594 A1 Apr. 1, 2010

(30) Foreign Application Priority Data
Jan. 22, 2007 (KR) .................. 10-2007-0006594

(51) Int. Cl.
*C09K 19/00* (2006.01)
*C09K 19/06* (2006.01)
*C09K 19/32* (2006.01)
*C09K 19/52* (2006.01)

(52) U.S. Cl. ............ 252/299.6; 252/299.01; 252/299.61; 252/299.62; 252/299.63; 252/299.64; 252/299.65; 252/299.66; 252/299.67; 430/20; 428/1.1; 428/1.3; 556/416; 556/432; 349/167; 349/182

(58) Field of Classification Search ............. 252/299.01, 252/299.6–299.67; 428/1.1, 1.3; 430/20; 556/416, 432; 349/167, 182
See application file for complete search history.

(56) References Cited

U.S. PATENT DOCUMENTS

| | | | |
|---|---|---|---|
| 7,700,000 B2 * | 4/2010 | Cheong et al. | 252/299.01 |
| 2004/0222403 A1 | 11/2004 | Sasada et al. | |
| 2008/0003382 A1 | 1/2008 | Oomori et al. | |
| 2010/0051867 A1 * | 3/2010 | Cheong et al. | 252/299.66 |
| 2010/0059712 A1 * | 3/2010 | Cheong et al. | 252/299.62 |

FOREIGN PATENT DOCUMENTS

| | | | |
|---|---|---|---|
| JP | 02004117890 A * | 4/2004 | |
| JP | 02004177737 A * | 6/2004 | |
| JP | 2005-281171 A | 10/2005 | |
| WO | WO 2006/115112 A1 | 11/2006 | |

* cited by examiner

*Primary Examiner* — Geraldina Visconti
(74) *Attorney, Agent, or Firm* — McKenna Long & Aldridge LLP

(57) ABSTRACT

Disclosed are a biaxial liquid crystal compound, a liquid crystal composition comprising the same, and an optical film using the same liquid crystal composition. More particularly, there is provided a liquid crystal material of a viewing angle compensation film with high quality characteristics, which can improve a contrast ratio and minimize variations in color with viewing angles in a black state, a liquid crystal composition comprising the same liquid crystal material, and a compensation film obtained from the same liquid crystal composition.

14 Claims, 1 Drawing Sheet

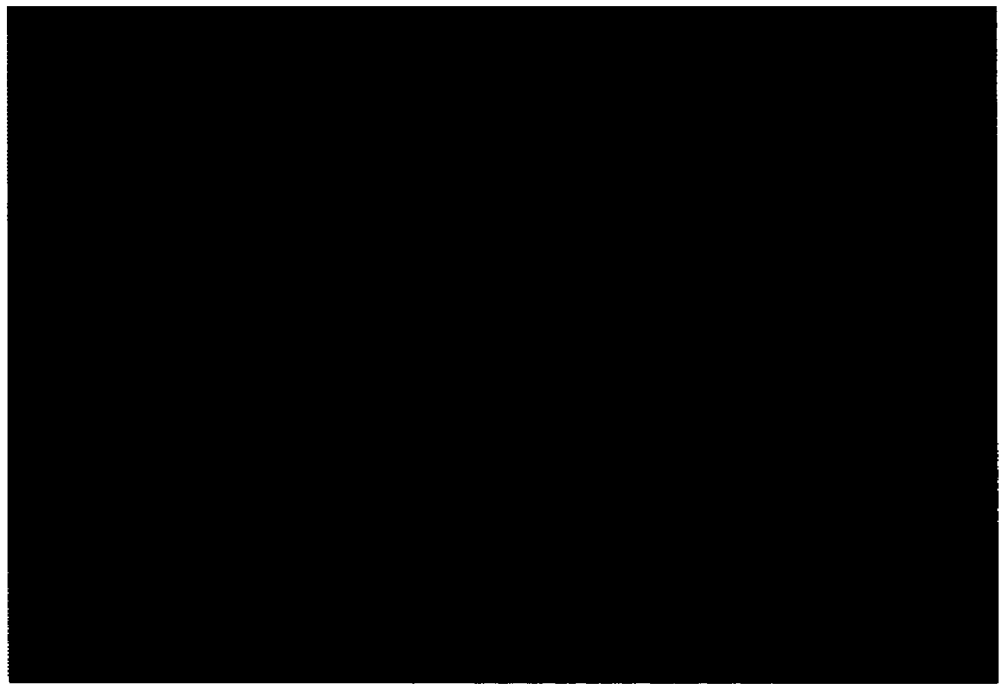

BIAXIAL LIQUID CRYSTAL COMPOUND, LIQUID CRYSTAL COMPOSITION COMPRISING THE SAME, AND OPTICAL FILM USING THE SAME LIQUID CRYSTAL COMPOSITION

This application claims the benefit of PCT/KR2008/000390 filed on Jan. 22, 2008, and Korean Patent Application No. 10-2007-0006594 filed on Jan. 22, 2007, both of which are hereby incorporated herein by reference for all purposes in their entirety.

TECHNICAL FIELD

The present invention relates to a biaxial liquid crystal compound, a liquid crystal composition comprising the same, and an optical film using the same liquid crystal composition.

BACKGROUND ART

Recently, as markets on watches, notebook PCs, cellular phones, televisions and monitors have been tremendously extended, the demand for displays of low weight and low power consumption has been greatly increased. A liquid crystal display (LCD), which is light and thin and requires low power consumption, has been widely applied to such products.

However, an LCD has a disadvantage of viewing angle dependency. In other words, an LCD shows variations in color or light/darkness depending on viewing directions or angles. Also, as a size of such an LCD increase, a viewing angle decreases. As compared to a conventional CRT (cathode ray tube) device having a viewing angle of about 180°, a TFT-LCD with no viewing angle compensation shows a viewing angle of merely about ±50°.

In order to solve the above described problems, various methods have been used, such methods including a multi-domain method in which pixels are divided in liquid crystal cells to control liquid crystal alignment, a method of controlling voltage, and a method of utilizing an optical compensation film.

The above-mentioned viewing angle dependency of an LCD is caused by the incident light having a tilt angle to an LCD panel, which shows a birefringence effect different from that of the vertical incident light. In order to compensate for this, a method of using an optical compensation film has been widely used, in which retardation films having opposite birefringence indexes to a panel are attached onto both surfaces of the panel. Also, as the size of a display panel has increased, a high-quality liquid crystal compensation film has been needed.

A retardation film is obtained by coating an aligned transparent support with liquid crystal, and aligning the liquid crystal along a predetermined direction to the direction of an aligning layer, followed by curing. After aligning, the liquid crystal has a direction opposite to the direction of liquid crystal cells upon application of voltage, so that light leakage in a black state can be minimized. When such retardation films are combined with a liquid crystal panel so that light is allowed to penetrate through the panel, it is possible to compensate for a light phase difference caused by a difference of light paths because paths of the incident light are similar to each other in all directions. In addition, it is also possible to perform compensation of a difference in birefringence indexes in upper/lower/left/right directions by optimizing the magnitude of birefringence of each film, an angle formed between films, a rubbing direction and an angle to a polarizer.

Therefore, there is a need for a new liquid crystal compound used for manufacturing a viewing angle compensation film having high-quality characteristics of improving a contrast ratio, and minimizing color variations in a black state depending on viewing angles.

DISCLOSURE OF THE INVENTION

Therefore, the present invention has been made in view of the above-mentioned problems, and provides a novel compound useful as a material for a viewing angle compensation film that can improve a contrast ratio and minimize variations in color with viewing angles in a black state.

Also, the present invention provides a liquid crystal composition comprising such a compound, and an optical film using the same liquid crystal composition.

In accordance with an aspect of the present invention, there is provided a novel biaxial liquid crystal compound. In accordance with another aspect of the present invention, there is provided a liquid crystal composition comprising the above biaxial liquid crystal compound, and an optical film using the same liquid crystal composition. In accordance with yet another aspect of the present invention, there is provided a liquid crystal display including the above optical film.

The novel biaxial liquid crystal compound according to the present invention is a compound represented by the following Formula 1:

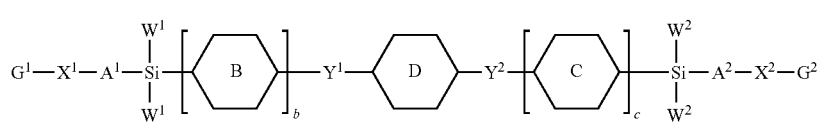

[Formula 1]

wherein $G^1$ and $G^2$ are each independently

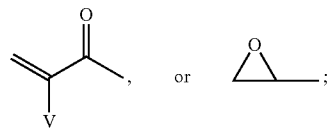

V is —H, —CH$_3$, —CH$_2$CH$_3$, —F, —Cl, —Br, or —CF$_3$;
$X^1$ and $X^2$ are each independently —O—, —NH—, a $C_1$~$C_{12}$ alkylene, or a single bond;
$A^1$ and $A^2$ are each independently a $C_1$~$C_{12}$ alkylene, a $C_2$~$C_{12}$ alkenylene, —(CH$_2$CH$_2$O)$_n$—, —(CH$_2$CHCH$_3$O)$_n$—, or —(CHCH$_3$CH$_2$O)$_n$—, and n is an integer of 1 to 5;
$W^1$ and $W^2$ are each independently —H, —CH$_3$, —CH$_2$CH$_3$, or —C$_6$H$_5$;
$Y^1$ and $Y^2$ are each independently —O—, —NR—, a $C_1$~$C_{18}$ alkylene, —CH=CH—, —C≡C—, —(CH$_2$)$_o$C(=O)O(CH$_2$)$_p$—, —(CH$_2$)$_o$OC(=O)(CH$_2$)$_p$—, —(CH$_2$)$_o$C(=O)(CH$_2$)$_p$—, —(CH$_2$)$_o$C(=O)NR(CH$_2$)$_p$—, —(CH$_2$)$_o$ $NRC(=O)(CH_2)_p$—, a single bond, —$SiH_2$—, —$SiMe_2$-, —$SiEt_2$-, —$CH_2SiH_2$—, —$CH_2SiMe_2$-, —$CH_2SiEt_2$-, —$SiH_2CH_2$—, —$SiMe_2CH_2$—, or —$SiEt_2CH_2$—;

o and p are each independently an integer of 0 to 2;

R is H, a $C_1$~$C_{20}$ alkyl, a $C_2$~$C_{20}$ alkenyl, or a $C_2$~$C_{20}$ alkynyl;

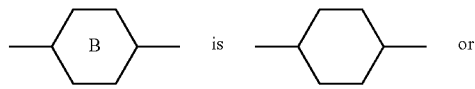

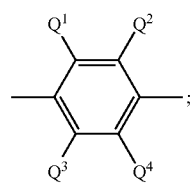

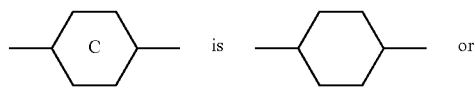

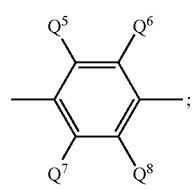

b and c are each independently an integer of 0 to 2;

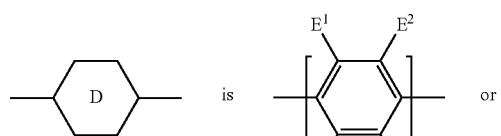

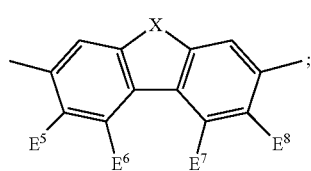

$Q^1$~$Q^8$ and $E^1$~$E^8$ are each independently —H, —F, —Cl, —Br, —I, —CN, —$CF_3$, —OH, —$CH_3$, —$CH_2CH_3$, —$C(=O)R^1$, —$CH=CHCO_2R^1$, -Ph-J, —C≡C-Ph-J, or —C≡C—$C(=O)R^1$, where $R^1$ is —$CH_3$, —$CH_2CH_3$, -Ph-J, or —C≡C-Ph-J;

J is —H, —F, —Cl, —Br, —I, —CN, —$CF_3$, —OH, —$CH_3$, —$CH_2CH_3$, —$OCH_3$, or —$OCH_2CH_3$, and is para-positioned to Ph;

e is an integer of 1 or 2; and

X is $CH_2$, $CHCH_3$, $C(CH_3)_2$, $CHC_2H_5$, $C(C_2H_5)_2$, $C(=O)$, NH, $NCH_3$, $NC_2H_5$, O, $SiH_2$, $Si(CH_3)_2$, or $Si(C_2H_5)_2$.

BRIEF DESCRIPTION OF THE DRAWINGS

The foregoing and other objects, features and advantages of the present invention will become more apparent from the following detailed description when taken in conjunction with the accompanying drawings in which:

FIG. 1 is a photograph taken by a polarizing microscope in a black state when a compensation film manufactured according to Example 5 of the present invention is used.

BEST MODE FOR CARRYING OUT THE INVENTION

The inventive compound represented by Formula 1, that is, the novel biaxial liquid crystal compound, is a polymerizable compound.

More specially, the biaxial liquid crystal compound of the present invention is a compound in which a polymerizable group as a substituent is introduced into either end of a biaxial mesogenic core. However, when a polymerizable group is directly attached to a mesogenic core, it is difficult to maintain an alignment state in polymerization. Therefore, a linking group is introduced between the mesogenic core and the polymerizable group.

In Formula 1, [ring B]$_b$-$Y^1$-ring D-$Y^2$-[ring C]$_c$ represents a mesogenic core, $G^1$ and $G^2$ represent polymerizable groups, and Si-$A^1$-$X^1$ and Si-$A^2$-$X^2$ represent linking groups.

An optical film fabricated using the compound represented by Formula 1, that is, the novel biaxial liquid crystal compound, shows a UV abnormal distribution. In other words, when UV dispersion is measured for the fabricated optical film, nd(450 nm)/nd(650 nm) has a value of <1.

Also, by introducing Si into the compound represented by Formula 1, the workability (physical properties) of the liquid crystal compound can be improved.

The inventive compound represented by Formula 1 is easily mixed with various liquid crystal materials, and has high solubility even at a low temperature. Further, the inventive compound is physically/chemically stable and has good heat/light stability under the conditions where a liquid crystal display is usually used, and can be a superior material constituting a liquid crystal composition because it forms a liquid crystal mesophase at a preferred range of temperatures. Further, a conventional liquid crystal composition shows a tendency to be precipitated as crystals at room temperature, but a liquid crystal composition comprising the inventive compound represented by Formula 1 does not show such crystal precipitation, even when kept for a week or more.

Therefore, the compound represented by Formula 1 is a liquid crystal compound applicable to an optical film that improves a wide viewing angle characteristic in a variety of liquid crystal displays.

In Formula 1, the $C_2$~$C_{12}$ alkenylene as $A^1$ and the $C_2$~$C_{12}$ alkenylene as $A^2$ may be each independently selected from the group consisting of —CH=CH—, —CH=$CCH_3$—, —$CH_2$CH=CH—, —CH=CH$CH_2CH_2$—, —$CH_2$CH=CH$CH_2$—, —$CH_2CH_2$CH=CH—, —CH=CH$CH_2CH_2CH_2$—, —$CH_2$CH=CH$CH_2CH_2$—, —$CH_2CH_2$CH=CH$CH_2$—, and —$CH_2CH_2CH_2$CH=CH—.

More specially, the compound represented by Formula 1 may be expressed by the following exemplary compounds, but the scope of the present invention is not limited thereto:

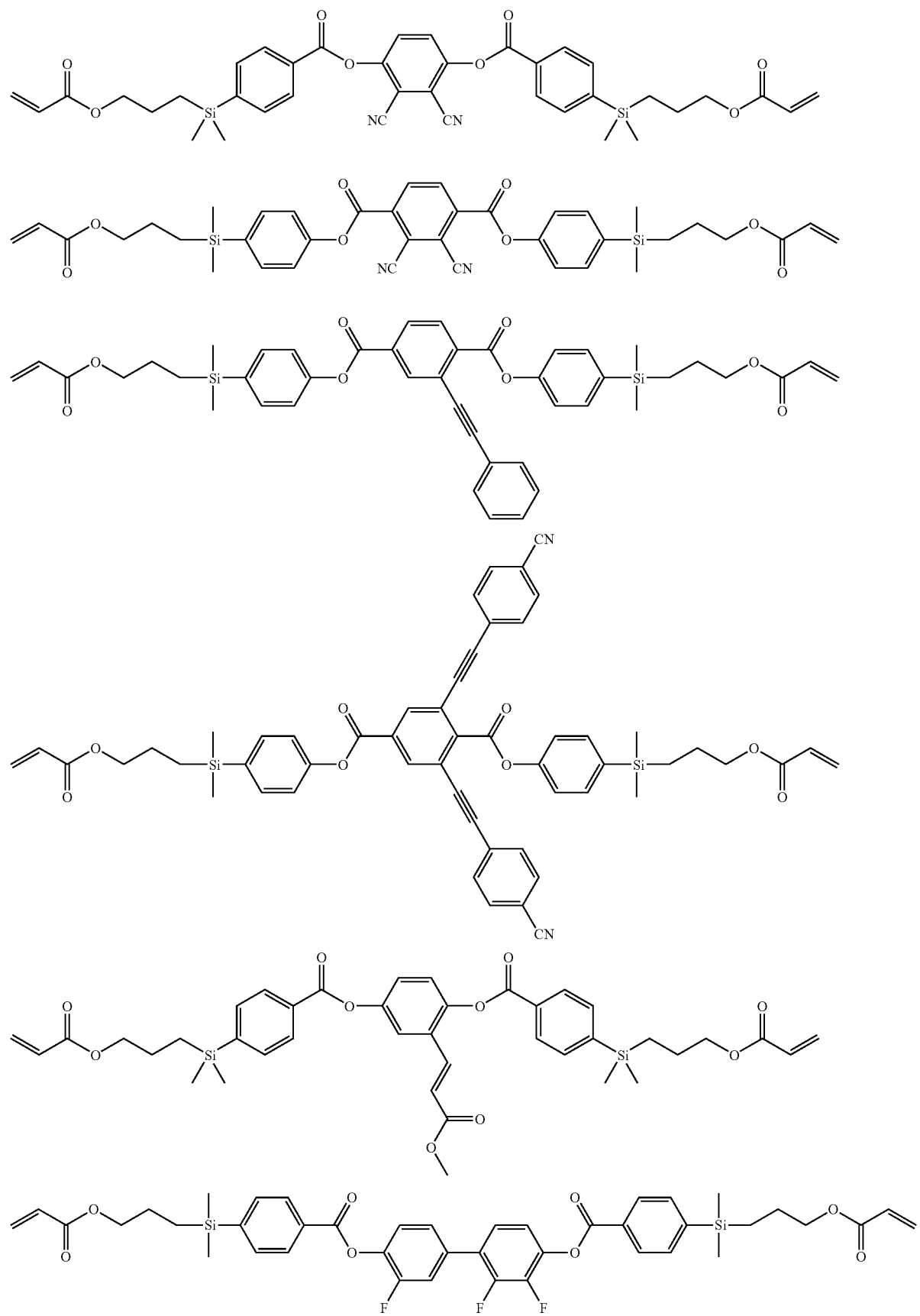

-continued

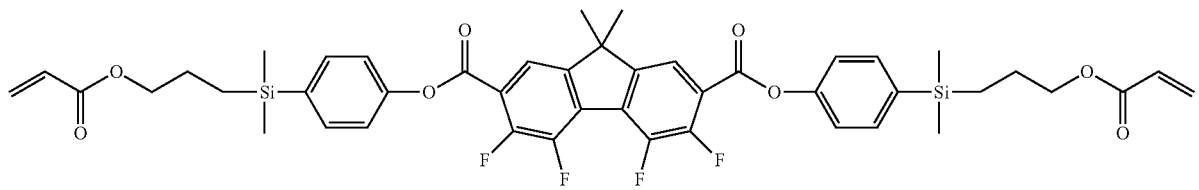

Reference will now be made to methods of preparing the compound represented by Formula 1, in connection with the following reaction schemes. However, the following reaction schemes are merely illustrative, and not meant to limit methods of preparing the compound of the present invention.

The compound represented by Formula 1 may be prepared by way of the following Reaction Scheme 1:

mulas 2 and 3 in Reaction Scheme 1 or esterification of the compounds represented by Formulas 4 and 5 in Reaction Scheme 2. Non-limiting examples of reagents used in the esterification include DCC (dicyclohexylcarbodiimide), EDC (1-ethyl-3-(3-(dimethylamino)propyl)carbodiimide), $SOCl_2$, $COCl_2$, MsCl (mesyl chloride), or the like, but the

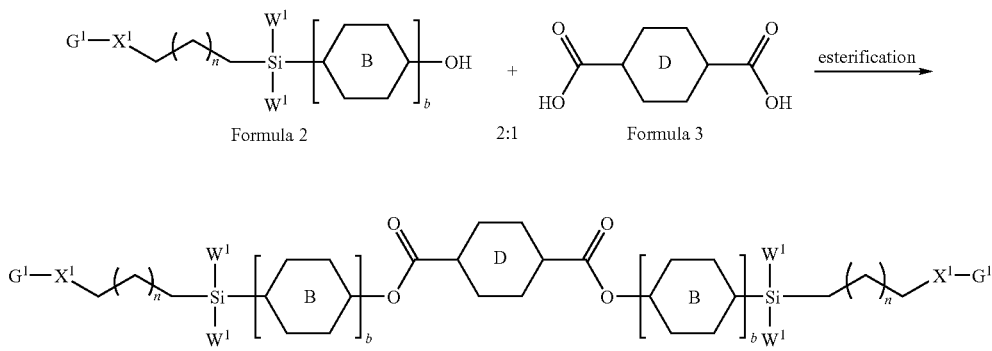

Also, the compound represented by Formula 1 may be prepared by way of the following Reaction Scheme 2:

present invention is not limited thereto, and other reagents well known in the art may also be used.

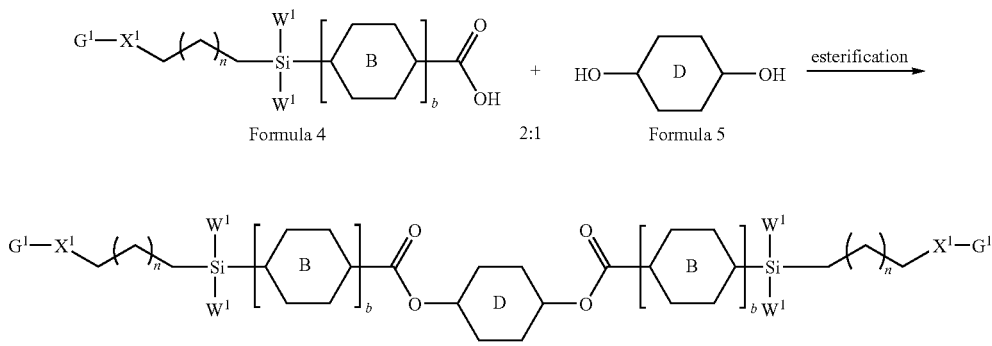

In Reaction Schemes 1 and 2, $G^1$, $X^1$, $W^1$, ring B, ring D, and b are the same as defined above in Formula 1, and n is an integer of 1 to 10.

The compound represented by Formula 1 may be synthesized by esterification of the compounds represented by For- With regard to this, the compound represented by Formula 2 in Reaction Scheme 1 may be prepared by way of the following Reaction Scheme 3, and the compound represented by Formula 4 in Reaction Scheme 2 may be prepared by way of the following Reaction Scheme 4:

[Reaction Scheme 3]

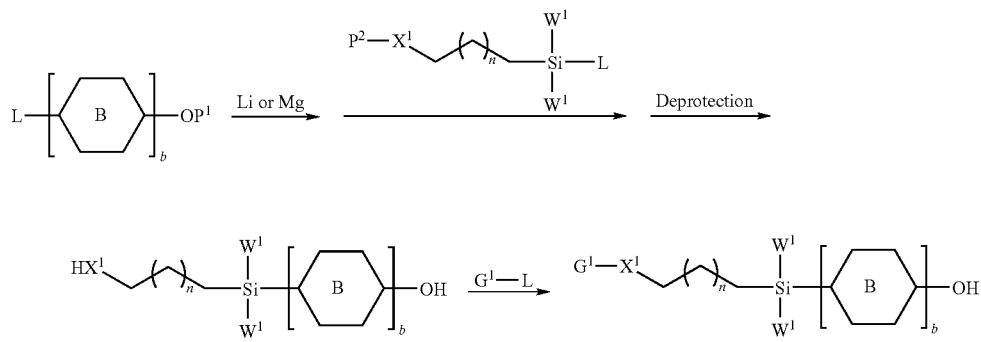

[Reaction Scheme 4]

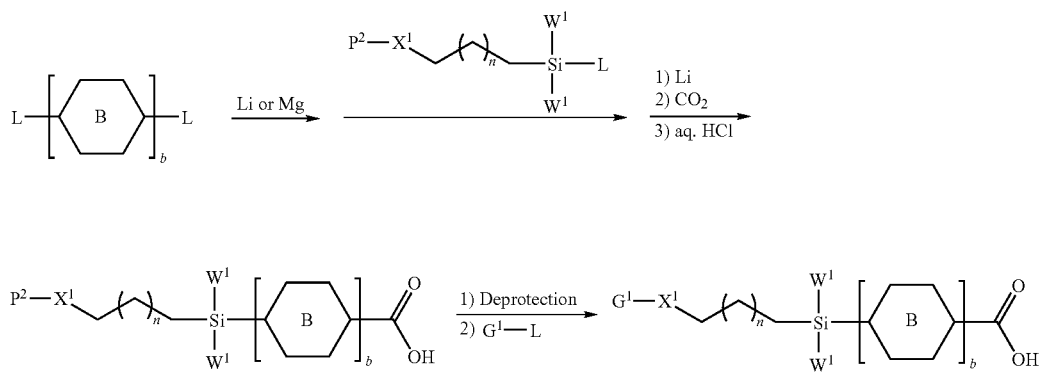

In Reaction Schemes 3 and 4, L is a leaving group, and its non-limiting examples include halides, mesylate (—OSO$_2$CH$_3$), tosylate (—OSO$_2$C$_6$H$_4$-p-CH$_3$), or the like, but the present invention is not limited thereto. Also, P$^1$ and P$^2$ are each independently a protecting group, and its non-limiting example include THP (tetrahydropyranyl), TBS (t-butyldimethylsiltl), etc., but the present invention is not limited thereto. Also, G$^1$, X$^1$, W$^1$, ring B, and b are the same as defined above in Formula 1, and n is an integer of 1 to 10.

When lithiation using Li is employed in Reaction Schemes 3 and 4, reagents other than Li, such as BuLi, may be used without any particular limitation, so long as they can conduct lithiation. In addition, the deprotection step may be conducted using reagents well known in the art.

The silicon derivative that is added as a reactant in the second step of each of Reaction Schemes 3 and 4 may be prepared by way of the following Reaction Scheme 5:

[Reaction Scheme 5]

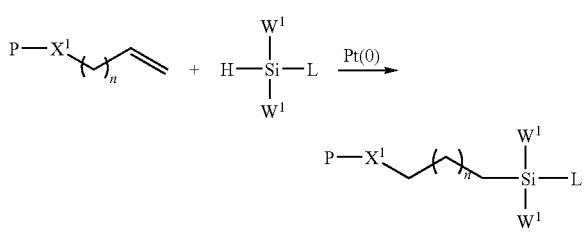

In Reaction Scheme 5, when X is —O— or —NH—, P is P$^1$ or P$^2$, and when X is a C$_1$~C$_{12}$ alkylene or a single bond, P is L, wherein P$^1$, P$^2$, and L are the same as defined above in Reaction Schemes 3 and 4.

In addition, the compound represented by Formula 1 may also be prepared by way of the following Reaction Scheme 6:

[Reaction Scheme 6]

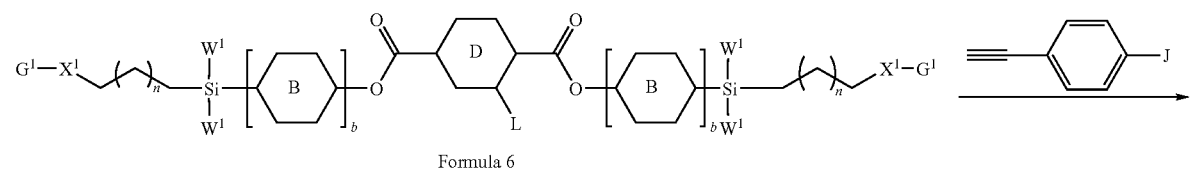

Formula 6

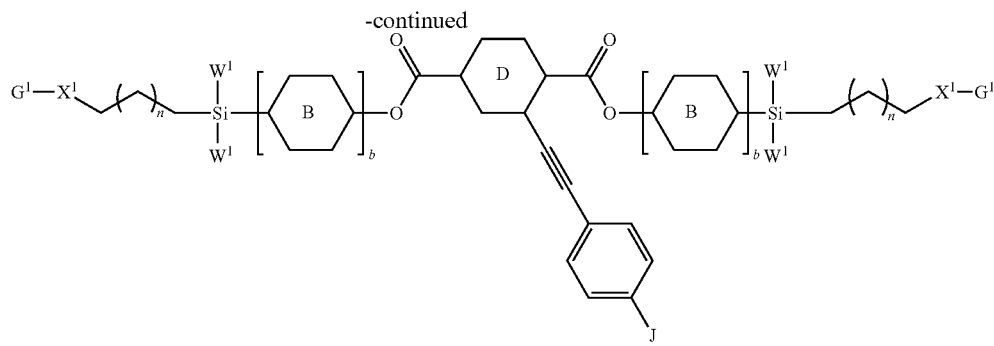

In Reaction Scheme 6, the compound represented by Formula 1 can be synthesized by coupling phenylacetylene with the compound represented by Formula 6 and using palladium (Pd) as a catalyst. In reaction Scheme 6, L is halides, $G^1$, $X^1$, $W^1$, J, ring B, ring D, and b are the same as defined above in Formula 1, and n is an integer of 1 to 10.

The above-mentioned methods of preparing the compound represented by Formula 1 also cover preparation methods via similar reaction paths to Reaction Schemes 1 to 6.

The present invention also provides a liquid crystal composition comprising the compound represented by Formula 1.

The compound represented by Formula 1 may be included in the liquid crystal composition in an amount of 0.1~99.9 wt %, preferably of 1~80 wt %, based on the total weight of the composition.

In addition to the above liquid crystal compound represented by Formula 1, the liquid crystal composition according to the present invention may include other various compounds, which can be mixed without disturbing liquid crystal properties. Examples of such compounds include a polymerizable liquid crystal compound, a polymerizable non-liquid crystal compound, and a polymer, which are currently used in a conventional liquid crystal composition, and may be used at various ratios as desired. It is preferable that each of the polymerizable compounds has a polymerizable group, such as a vinyl group, a vinyloxy group, an acrylic group, or a methacrylic group.

The liquid crystal composition according to the present invention may include a photoreaction initiator as required, and herein, the photoreaction initiator may include conventional initiators known in the art without any particular limitation. Non-limiting examples of the photoreaction initiator include benzoyl ether, benzoyl isobutyl ether, benzoyl isopropyl ether, benzophenone, acetophenone, 4-benzoyl-4'-methyl diphenyl sulfide, benzyl methyl ketal, dimethylamino methyl benzoate, 3,3'-dimethyl-4-methoxybenzophenone, methyl benzoylformate, 2-methyl-1-(4-methylthio)phenyl)-2-morpholinopropane-1-one, 2-benzyl-2-dimethylamino-1-(4-morpholinophenyl)-butane-1-one, 1-hydroxycyclohexyl phenyl ketone, Irgacure based, etc. Also, the photoreaction initiator may be added in an amount of 0.001 to 20 parts by weight, preferably 0.01 to 10 parts by weight, based on 100 parts by weight of a polymerizable liquid crystal compound.

Also, the liquid crystal composition according to the present invention may include an organic solvent as required. The inclusion of the organic solvent facilitates the application (coating) of the liquid crystal composition on a substrate such as a film.

Herein, as the organic solvent, conventional organic solvents known in the art may be used without any particular limitation. Non-limiting examples of the organic solvent include: hydrocarbons such as cyclohexane, cyclopentane, benzene, toluene, xylene, butylbenzene, etc.; ketones such as acetone, methyl ethyl ketone, methyl isobutyl ketone, cyclohexanone, etc.; esters such as ethyl acetate, ethylene glycol monomethyl ether acetate, propylene glycol monomethyl ether acetate, gamma-butyrolactone, etc.; amides such as 2-pyrrolidone, N-methyl-2-pyrrolidone, dimethyl formamide, dimethylacetamide, etc.; halogens such as chloroform, dichloromethane, carbon tetrachloride, dichloroethane, tetrachloroethane, tetrachloroethylene, chlorobenzene, etc.; alcohols such as t-butyl alcohol, diacetone alcohol, glycerin, monoacetin, ethylene glycol, triethylene glycol, hexylene glycol, ethylene glycol monomethyl ether, etc.; phenols such as phenol, parachlorophenol, etc.; and ethers such as methoxybenzene, 1,2-dimethoxybenzene, diethylene glycol dimethyl ether, ethylene glycol dimethyl ether, ethylene glycol diethyl ether, propylene glycol dimethyl ether, propylene glycol diethyl ether, diethylene glycol dimethyl ether, diethylene glycol diethyl ether, dipropylene glycol dimethyl ether, dipropylene glycol diethyl ether, etc. Also, such an organic solvent can be independently used, or can be used by mixing at least two of these materials, and herein, the usage amount is not limited.

Also, the liquid crystal composition according to the present invention may include a surfactant as required. A surfactant allows a liquid crystal composition to be easily applied on a substrate. As the surfactant, conventional surfactants known in the art may be used without any particular limitation, and the additional amount varies according to the kind of surfactant, the composition ratio of components of a liquid crystal composition, the kind of solvent, and the kind of substrate.

Also, the liquid crystal composition according to the present invention may include a chiral dopant or a leveling agent that prevents distortion of a spiral structure of liquid crystal or reverse distortion of liquid crystal, etc. as an additional additive.

The liquid crystal composition according to the present invention may be prepared in a conventional manner. Typically, in the preparation, various components are dissolved at room temperature or high temperature.

The present invention provides an optical film using the liquid crystal composition according to the present invention.

The optical film according to the present invention is manufactured by forming an optically anisotropic layer, that is, a liquid crystal film, on a substrate. Herein, a liquid crystal alignment state in the liquid crystal film can be adjusted by appropriately selecting a polymerizable liquid crystal compound forming a liquid crystal composition, and other compounds.

Non-limiting examples of the optical film according to the present invention include an A-plate type compensation film, a B-plate type compensation film, a (+)C-plate type compensation film, a (−)C-plate type compensation film, or a compensation film showing abnormal UV dispersion, etc.

In the optical film of the present invention, the substrate may be used without any particular limitation, so long as the liquid crystal film can be formed on its surface. Examples of such the substrate include a polymer film, a metal, or a glass, etc.

Non-limiting examples of the polymer film include polyimide, polyamide imide, polyamide, polyetherimide, polyetheretherketone, polyetherketone, polyketone sulfide, polyethersulfone, cycloolefin polymer, polysulfone, polyphenylene sulfide, polyphenylene oxide, polyethylene terephthalate, polybutylene terephthalate, polyethylene naphthalate, polyacetal, polycarbonate, polyacrylate, acrylic resin, polyvinyl alcohol, polypropylene, cellulose, triacetyl cellulose, epoxy resin, phenol resin, etc., and herein the examples may be a uniaxially oriented film or a biaxially oriented film. Also the polymer film may be used after surface treatment such as hydrophilic treatment or hydrophobic treatment, and may be a laminated film. Also, non-limiting examples of the metal include aluminum, iron, copper, etc., which have slit-shaped surface grooves; and non-limiting examples of the glass include alkali glass, boric glass, print glass, etc., which have slit-shaped surfaces through etching.

Also, the substrate may have an alignment layer thereon. Non-limiting examples of a material for the alignment layer include polyimide, polyamide, polyacrylate, polyvinyl alcohol, etc.

Some of the substrate materials can be directly used due to sufficient capability of aligning a liquid crystal compound. However, in order to enhance alignment capability, the substrate materials may be subjected to separate treatment, such as rubbing, stretching, polarization irradiation, or skew ray irradiation, before being used as the substrate.

Herein, the rubbing can be directly performed on a substrate, or can be performed on an alignment layer previously formed on a substrate.

The optical film according to the present invention may be fabricated by common methods well known in the art. As an example, the optical film of the present invention may be fabricated by coating the inventive liquid crystal composition on a substrate, drying the coated liquid crystal composition to thereby aligning the liquid crystal compound, and then curing the aligned liquid crystal compound while maintaining the alignment form of the liquid crystal compound to thereby fix the alignment form.

The coating of a liquid crystal composition on a substrate may be performed in a conventional manner. Non-limiting examples of such a coating include spin coating, roll coating, printing, dip-drawing coating, curtain coating, die coating, dip coating, etc.

The drying process may be performed in a conventional manner, and herein, a liquid crystal compound is aligned during the drying process or is aligned by additionally heating after the drying process. The conditions of drying vary according to a boiling point of an organic solvent used for a liquid crystal composition, and materials for a substrate and an alignment layer, without any particular limitation. Also, it is possible to dry by heating, or to gradually dry at room or low temperature.

The curing process may be performed by irradiating rays and/or heat-treating on a coated liquid crystal composition. In the process, polymerization is carried out by a polymerizable group of a polymerizable compound, and a liquid crystal compound with a fixed alignment is attached on a substrate, thereby forming a liquid crystal film with an optically anisotropic layer. The wavelengths of the rays used for the curing process may include, but are not limited to, electron beams, ultraviolet rays, visible rays, infrared rays, etc. Also, the heat-treating is generally performed at 10~200° C. from 3 seconds to 30 minutes, but the conditions of the heat-treating are not limited to this.

Also, the optical film according to the present invention may be manufactured by coating a liquid crystal composition on a peelable film, drying the composition, forming a liquid crystal film through a curing process, and transferring the formed liquid crystal film to a substrate by using a gluing agent or adhesives.

The optical film according to the present invention may be used as an optical compensation film or a polarizer using the optical compensation film, and may be provided in a liquid crystal display.

Reference will now be made in detail to the preferred embodiments of the present invention. However, the following examples are illustrative only, and the scope of the present invention is not limited thereto.

EXAMPLE 1

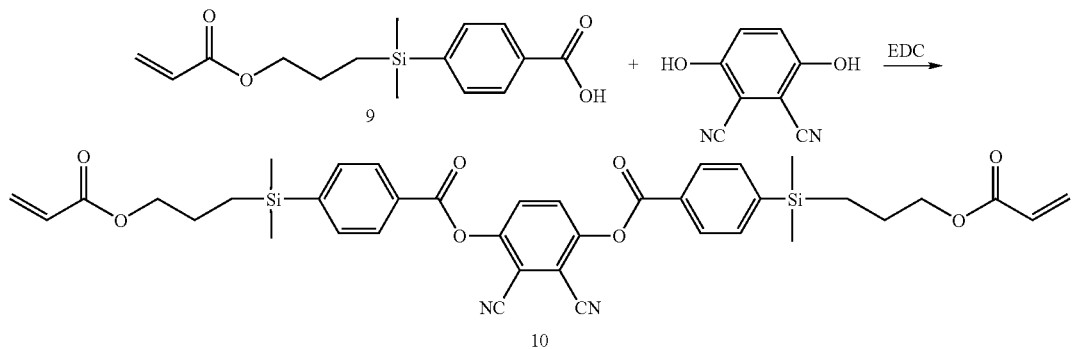

First, 2 equivalents of Compound 9 and 1 equivalent of 2,3-dicyanohydro quinine were dissolved in $CH_2Cl_2$ as a solvent, and the reaction mixture was subjected to a coupling reaction by using EDC. The reaction mixture was stirred at room temperature for about 20 hours, the resultant product was worked up with water and $CH_2Cl_2$, and then Compound 10 was finally obtained at a yield of 90% by using silica gel column chromatography. ¹HNMR (400 MHz, CDCl₃): δ 0.30 (s, 12H), 0.69~0.78 (m, 4H), 1.71~1.83 (m, 4H), 4.15 (t, 4H), 5.81 (d, 2H), 6.11 (dd, 2H), 6.39 (d, 2H), 7.08 (d, 4H), 7.82 (s, 2H), 8.38 (d, 4H).

EXAMPLE 2

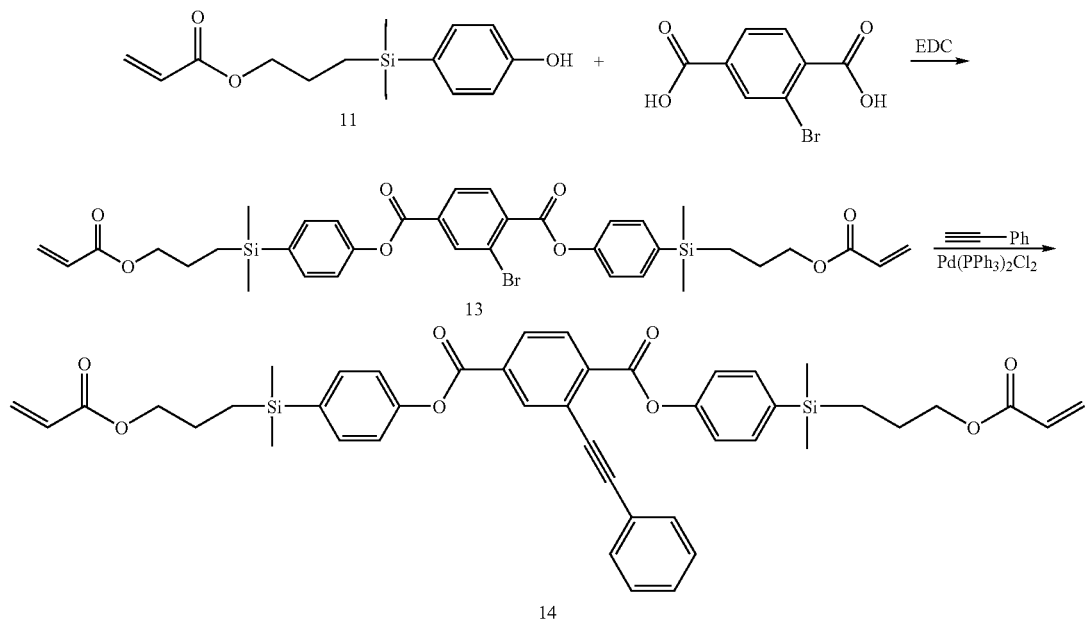

First, 2 equivalents of Compound 11 and 1 equivalent of bromoterephthalic acid were dissolved in CH₂Cl₂ as a solvent, and the reaction mixture was subjected to a coupling reaction by using EDC. The reaction mixture was stirred at room temperature for about 20 hours, the resultant product was worked up with water and CH₂Cl₂, and then Compound 13 was finally obtained at a yield of 88% by using silica gel column chromatography.

Subsequently, 1 equivalent of Compound 13 was dissolved in benzene as a solvent, 1.3 equivalents of phenylacetylene, 0.3 equivalents of palladium catalyst, 0.3 equivalents of CuI, and 1.3 equivalents of DBU were added thereto, and the reaction mixture was heated at about 80° C. for about 20 hours. The resultant product was worked up with water and ethyl acetate, was free from the solvent, and then was recrystallized from isopropyl alcohol to thereby finally obtain Compound 14 at a yield of 70%. ¹HNMR (400 MHz, CDCl₃): δ 0.28 (s, 12H), 0.71~0.79 (m, 4H), 1.70~1.85 (m, 4H), 4.13 (t, 4H), 5.82 (d, 2H), 6.11 (dd, 2H), 6.40 (d, 2H), 7.15 (d, 4H), 7.20~7.42 (m, 5H), 7.45 (d, 4H), 8.31 (d, 1H), 8.39 (d, 1H), 8.63 (s, 1H).

EXAMPLE 3

Liquid Crystal Composition 1

Liquid Crystal Composition 1 was prepared according to the following composition:

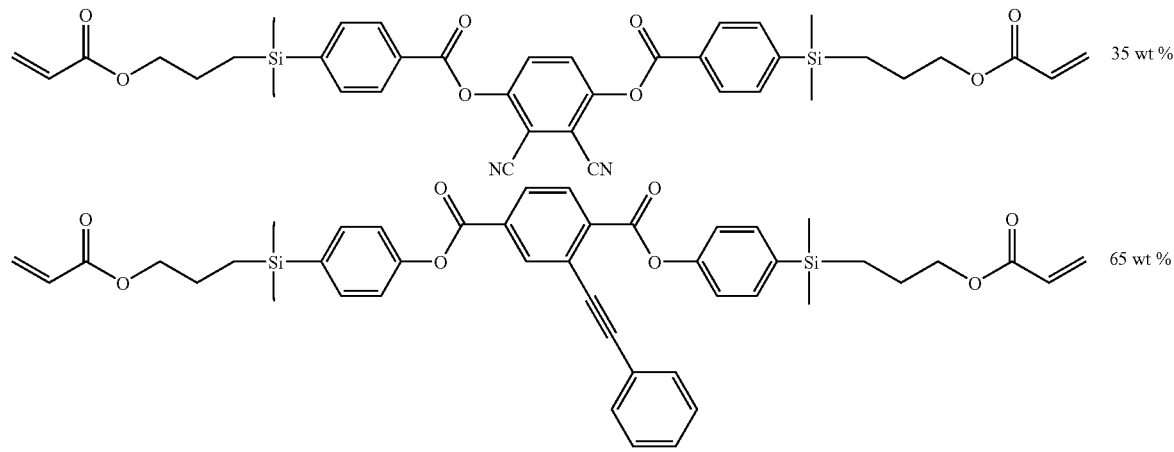

EXAMPLE 4

Liquid Crystal Composition 2

Liquid Crystal Composition 2 was prepared according to the following composition:

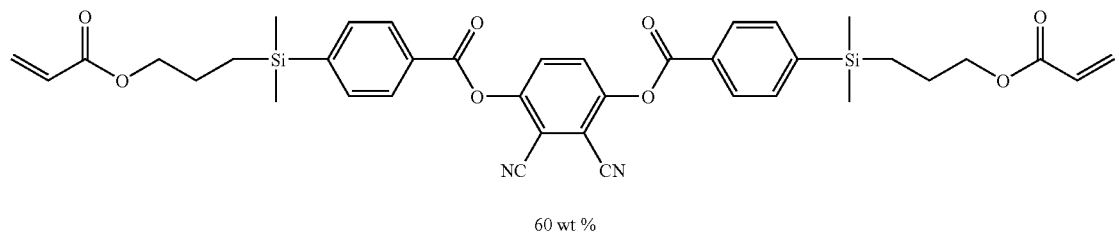

60 wt %

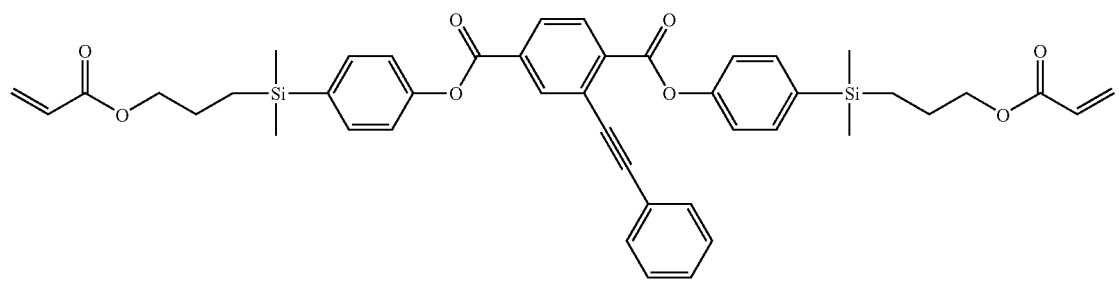

40 wt %

EXAMPLE 5

Fabrication of Compensation Film

First, 9.28 g of Liquid Crystal Composition 1 prepared according to Example 3 was dissolved in 30 g of cyclohexanone, 600 mg of Irgacure 907 (2-methyl-4'-(methylthio)-2-morpholinophenone), 40 mg of FC-4430 as an alignment promoter, and 80 mg of BYK-300 as a leveler were added thereto, and the reaction mixture was shaken sufficiently. After the reaction mixture was completely dissolved, a solution from which particles were removed was prepared using a particle filter. An LCD glass that had been treated with an alignment layer was rubbed using a rubbing cloth, and then the resultant solution was spin-coated onto the LCD glass at 2000 rpm for 20 seconds. The coated LCD glass was dried in an oven at 90° C. for 1 minute, and then was subjected to UV (200 W~80 W/m) irradiation to thereby provide a compensation film.

EXAMPLE 6

Fabrication of Compensation Film

A compensation film was fabricated in the same manner as described in Example 5, except that Liquid Crystal Composition 2 prepared according to Example 4 was used instead of Liquid Crystal Composition 1 prepared according to Example 3.

COMPARATIVE EXAMPLE 1

Fabrication of +C Type Compensation Film

A +C type compensation film was fabricated in the same manner as described in Example 5, except that LC242 commercially available from BASF was used instead of Liquid Crystal Composition 1 prepared according to Example 3.

LC242 commercially available from BASF:

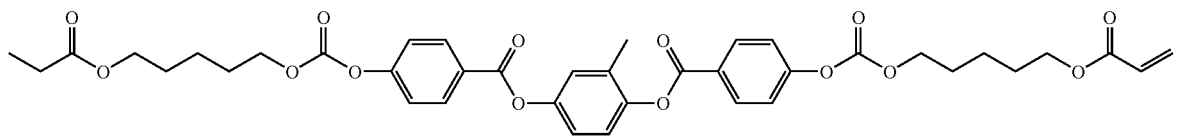

[Determination of Physical Properties of Compensation Films]

Each of the compensation films fabricated according to Example 5, Example 6, and Comparative Example 1 was determined for its thickness, refractive index, and retardation.

More specially, the thickness of the film was measured using a micro-gauge, and the refractive index and birefringence index of the film were measured at a mean wavelength of 550 nm by using an Abbe refractometer. Also, the wavelength dispersion value of the film was obtained from the ratio of 450 nm/650 nm, which was determined by measuring UV dispersion by means of Axo scan equipment. The results of the physical properties are shown below in Table 1.

TABLE 1

| compensation film | thickness (μm) | birefringence index (Δn) | wavelength dispersion value (450 nm/650 nm) |
|---|---|---|---|
| Ex. 5 | 1 | 0.078 | 0.89 |
| Ex. 6 | 1 | 0.091 | 0.95 |
| Com. Ex. 1 | 1 | 0.122 | 1.12 |

As a result of measuring the UV dispersion of the fabricated compensation films by using the Axo scan equipment, it was confirmed that the compensation film of Example 5 has a wavelength dispersion value (nd(450 nm)/nd(650 nm)) of 0.89, that is, a wavelength dispersion value less than 1, and thus shows abnormal dispersion. Also, it was confirmed that the compensation film of Example 6 has a wavelength dispersion value (nd(450 nm)/nd(650 nm)) of 0.95, that is, a wavelength dispersion value less than 1, and thus also shows abnormal dispersion. However, the compensation film of Comparative Example 1 has a wavelength dispersion value (nd(450 nm)/nd(650 nm)) of 1.12, that is, shows normal dispersion.

FIG. 1 illustrates a polarizing microscopic photograph of the compensation film fabricated according to Example 5, which is in a black state.

In general, a compensation film is used to prevent light leakage in a black state. Since the degree of black color in the black state is important in contrast and a viewing angle, it can be said that the purer the black color, the better the compensation film. Therefore, with reference to the pure black state photograph taken by a polarizing microscope shown in FIG. 1, the surface quality and the alignment state of the film according to Example 7 are determined, and accordingly, it is determined that the film has an excellent alignment state, and thus is suitable for an optical compensation film.

Industrial Applicability

As can be seen from the foregoing, the inventive biaxial liquid crystal compound and the inventive liquid crystal composition comprising the same can be characteristic of abnormal UV dispersion. Also, the inventive liquid crystal composition makes it possible to fabricate a viewing angle compensation film with high quality characteristics, which can improve a contrast ratio and minimize variations in color with viewing angles in a black state.

Although several exemplary embodiments of the present invention have been described for illustrative purposes, those skilled in the art will appreciate that various modifications, additions and substitutions are possible, without departing from the scope and spirit of the invention as disclosed in the accompanying claims.

The invention claimed is:
1. A compound represented by the following Formula 1:

[Formula 1]

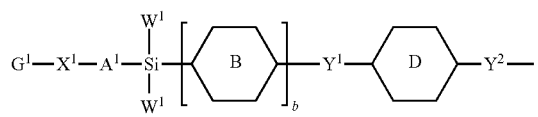

-continued

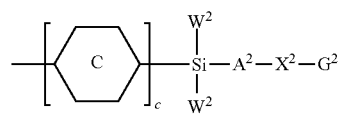

wherein $G^1$ and $G^2$ are each independently

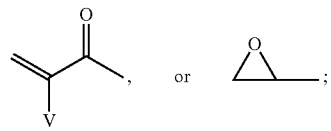

V is —H, —$CH_3$, —$CH_2CH_3$, —F, —Cl, —Br, or —$CF_3$;

$X^1$ and $X^2$ are each independently —O—, —NH—, a $C_1$~$C_{12}$ alkylene, or a single bond;

$A^1$ and $A^2$ are each independently a $C_1$~$C_{12}$ alkylene, a $C_2$~$C_{12}$ alkenylene, —($CH_2CH_2O$)$_n$—, —($CH_2CHCH_3O$)$_n$—, or —($CHCH_3CH_2O$)$_n$—, and n is an integer of 1 to 5;

$W^1$ and $W^2$ are each independently —H, —$CH_3$, —$CH_2CH_3$, or —$C_6H_5$;

$Y^1$ and $Y^2$ are each independently —O—, —NR—, a $C_1$~$C_{18}$alkylene, —CH=CH—, —C≡C—, —($CH_2$)$_o$C(=O)O($CH_2$)$_p$—, —($CH_2$)$_o$OC(=O)($CH_2$)$_p$—, —($CH_2$)$_o$C(=O)($CH_2$)$_p$—, —($CH_2$)$_o$C(=O)NR($CH_2$)$_p$—, —($CH_2$)$_o$NRC(=O)($CH_2$)$_p$—, a single bond, —$SiH_2$—, —$SiMe_2$-, —$SiEt_2$-, —$CH_2SiH_2$—, —$CH_2SiMe_2$-, —$CH_2SiEt_2$-, —$SiH_2CH_2$—, —$SiMe_2CH_2$—, or —$SiEt_2CH_2$—;

o and p are each independently an integer of 0 to 2;

R is H, a $C_1$~$C_{20}$ alkyl, a $C_2$~$C_{20}$ alkenyl, or a $C_2$~$C_{20}$ alkynyl;

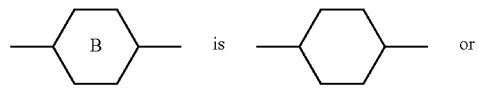

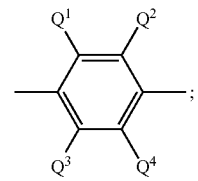

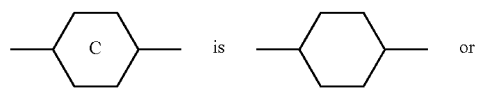

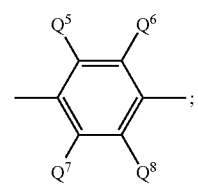

b represents 1 or 2;

c is an integer of 0 to 2;

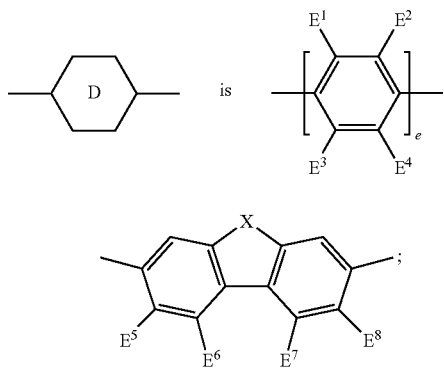

$Q^1$~$Q^8$ and $E^1$~$E^8$ are each independently —H, —F, —Cl, —Br, —I, —CN, —CF$_3$, —OH, —CH$_3$, —CH$_2$CH$_3$, —C(=O)R$^1$, —CH=CHCO$_2$R$^1$, -Ph-J, —C≡C-Ph-J, or —C≡C—C(=O)R$^1$, where R$^1$ is —CH$_3$, —CH$_2$CH$_3$, -Ph-J, or —C≡C-Ph-J;

J is —H, —F, —Cl, —Br, —I, —CN, —CF$_3$, —OH, —CH$_3$, —CH$_2$CH$_3$, —OCH$_3$, or —OCH$_2$CH$_3$, and is para-positioned to Ph;

e is an integer of 1 or 2; and

X is CH$_2$, CHCH$_3$, C(CH$_3$)$_2$, CHC$_2$H$_5$, C(C$_2$H$_5$)$_2$, C(=O), NH, NCH$_3$, NC$_2$H$_5$, O, SiH$_2$, Si(CH$_3$)$_2$, or Si(C$_2$H$_5$)$_2$.

2. The compound as claimed in claim 1, wherein the C$_2$~C$_{12}$ alkenylene as A$^1$ and the C$_2$~C$_{12}$ alkenylene as A$^2$ are each independently selected from the group consisting of —CH=CH—, —CH=CCH$_3$—, —CH$_2$CH=CH—, —CH=CHCH$_2$CH$_2$—, —CH$_2$CH=CHCH$_2$—, —CH$_2$CH$_2$CH=CH—, —CH=CHCH$_2$CH$_2$CH$_2$—, —CH$_2$CH=CHCH$_2$CH$_2$—, —CH$_2$CH$_2$CH=CHCH$_2$—, and —CH$_2$CH$_2$CH$_2$CH=CH—.

3. The compound as claimed in claim 1, which is prepared by way of the following Reaction Scheme 1:

[Reaction Scheme 1]

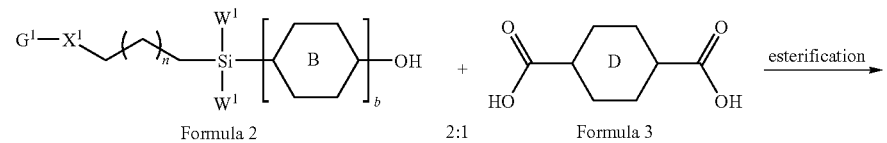

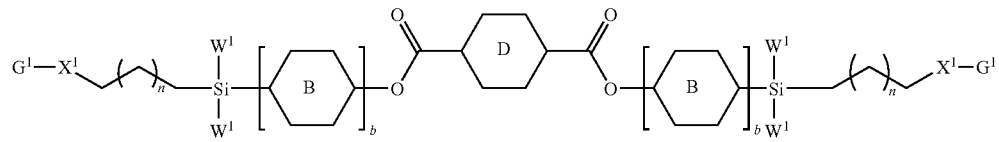

wherein G$^1$, X$^1$, W$^1$, ring B, ring D, and b are as defined in claim 1, and n is an integer of 1 to 10.

4. The compound as claimed in claim 3, wherein a compound represented by Formula 2 is prepared by way of the following Reaction Scheme 3:

[Reaction Scheme 3]

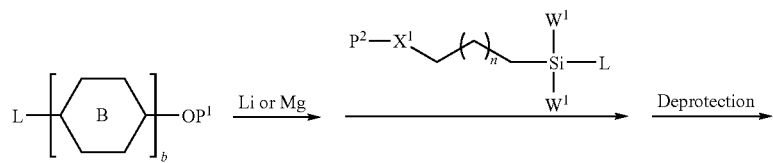

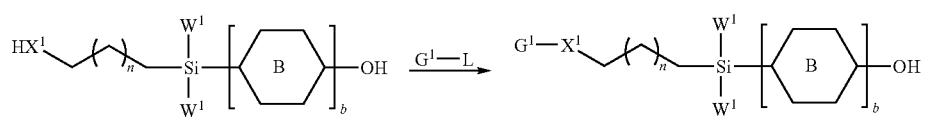

wherein $G^1$, $X^1$, $W^1$, ring B, and b are as defined in claim 1, L is a leaving group, $P^1$ and $P^2$ are each independently a protecting group, and n is an integer of 1 to 10.

5. The compound as claimed in claim 1, which is prepared by way of the following Reaction Scheme 2:

[Reaction Scheme 2]

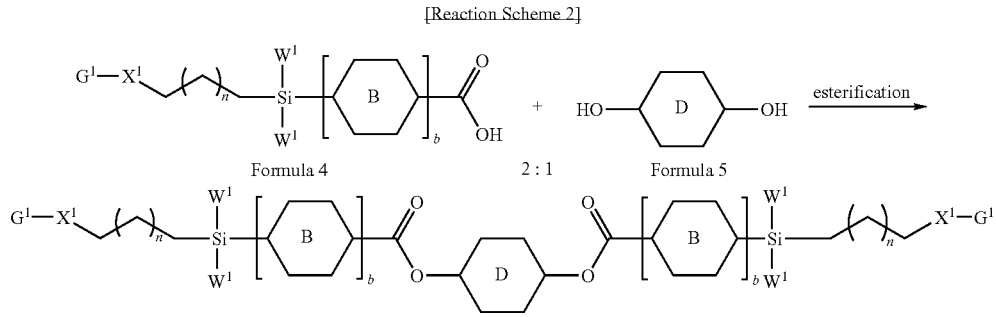

wherein $G^1$, $X^1$, $W^1$, ring B, ring D, and b are as defined in claim 1, and n is an integer of 1 to 10.

6. The compound as claimed in claim 5, wherein a compound represented by Formula 4 is prepared by way of the following Reaction Scheme 4:

[Reaction Scheme 4]

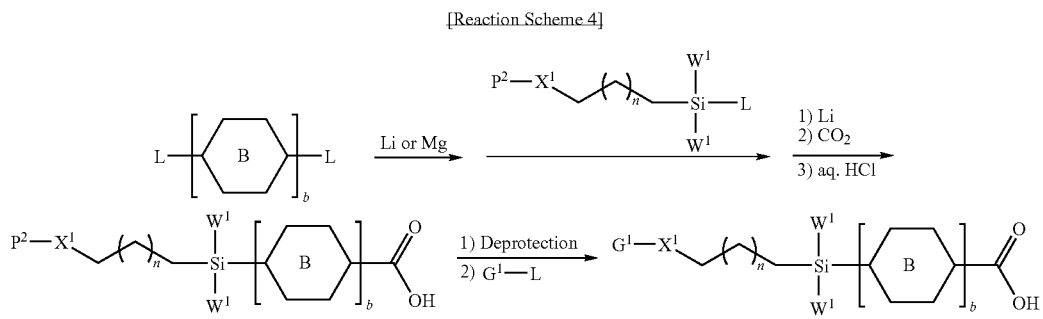

wherein $G^1$, $X^1$, $W^1$, ring B, and b are as defined in claim 1, L is a leaving group, $P^1$ is a protecting group, and n is an integer of 1 to 10.

7. The compound as claimed in claim 1, which is prepared by way of the following Reaction Scheme 6:

[Reaction Scheme 6]

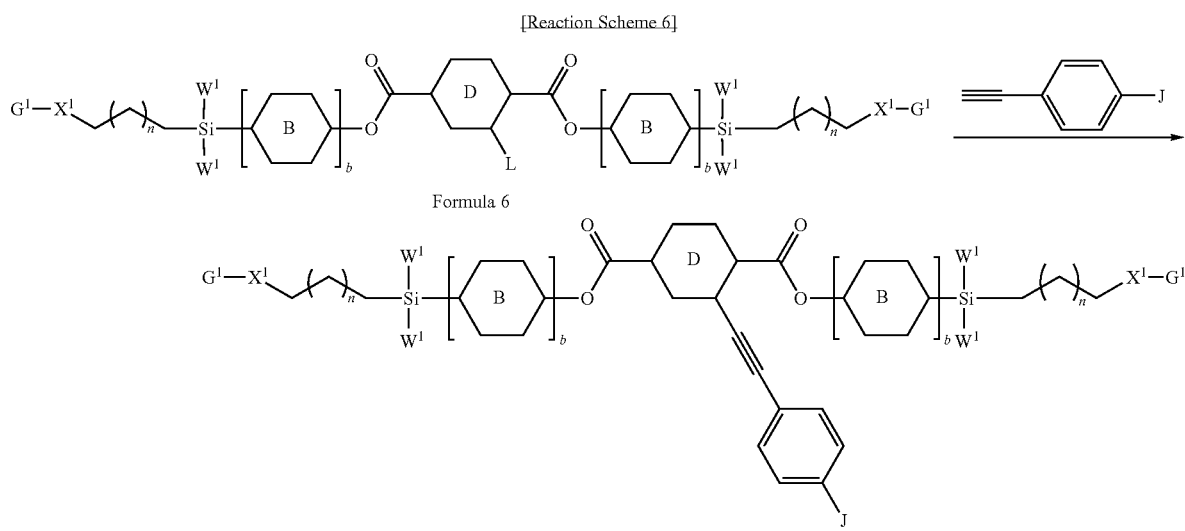

wherein L is a halide, $G^1$, $X^1$, $W^1$, J, ring B, ring D, and b are as defined in claim 1, and n is an integer of 1 to 10.

8. A liquid crystal composition comprising the compound represented by Formula 1 of claim 1.

9. The liquid crystal composition as claimed in claim 8, wherein the compound represented by Formula 1 is included in the liquid crystal composition in an amount of 1 to 80 wt % based on the total weight of the liquid crystal composition.

10. An optical film using a liquid crystal composition comprising the compound represented by Formula 1 of claim 1.

11. The optical film as claimed in claim 10, which is an A-plate compensation film, a B-plate compensation film, a (+)C-plate compensation film, a (−) C-plate compensation film, or a compensation film showing abnormal UV dispersion.

12. A liquid crystal display comprising the optical film as claimed in claim 10.

13. The optical film as claimed in claim 10, wherein the compound represented by Formula 1 is included in the liquid crystal composition in an amount of 1 to 80 wt % based on the total weight of the liquid crystal composition.

14. The liquid crystal display as claimed in claim 12, wherein the compound represented by Formula 1 is included in the liquid crystal composition in an amount of 1 to 80 wt % based on the total weight of the liquid crystal composition.

* * * * *